(12) United States Patent
McHugh et al.

(10) Patent No.: US 9,844,438 B2
(45) Date of Patent: Dec. 19, 2017

(54) FEMORAL STEM WITH PARTIALLY RECESSED POROUS COATING

(71) Applicant: Joint Development, LLC, Salt Lake City, UT (US)

(72) Inventors: Dermott J. McHugh, Seattle, WA (US); Eric M. Dacus, Salt Lake City, UT (US)

(73) Assignee: Joint Development, LLC, Salt Lake City, UT (US)

( * ) Notice: Subject to any disclaimer, the term of this patent is extended or adjusted under 35 U.S.C. 154(b) by 0 days.

(21) Appl. No.: 15/250,791

(22) Filed: Aug. 29, 2016

(65) Prior Publication Data
US 2017/0056184 A1 Mar. 2, 2017

Related U.S. Application Data

(60) Provisional application No. 62/211,572, filed on Aug. 28, 2015.

(51) Int. Cl.
*A61F 2/36* (2006.01)
*A61F 2/30* (2006.01)

(52) U.S. Cl.
CPC .......... *A61F 2/367* (2013.01); *A61F 2/30767* (2013.01); *A61F 2002/30013* (2013.01); *A61F 2002/30769* (2013.01); *A61F 2002/30805* (2013.01); *A61F 2002/369* (2013.01)

(58) Field of Classification Search
CPC .... A61F 2/3662; A61F 2/367; A61F 2/30907; A61F 2002/30013; A61F 2002/30805; A61F 2002/369
See application file for complete search history.

(56) References Cited

U.S. PATENT DOCUMENTS

| | | | |
|---|---|---|---|
| 4,608,055 A | 8/1986 | Morrey et al. |
| 4,778,475 A | 10/1988 | Ranawat et al. |
| 4,828,566 A | 5/1989 | Griss |
| 4,938,772 A | 7/1990 | Frey et al. |
| 5,013,324 A | 5/1991 | Zolman et al. |

OTHER PUBLICATIONS

Zimmer, Inc., APS Natural-Hip System Surgical Technique (www.zimmer.com), 97-6710-002-00 Rev.1 5ML, 2008, 14 pages, Zimer, Inc., USA.

*Primary Examiner* — Brian Dukert
(74) *Attorney, Agent, or Firm* — Lowry Blixseth LLP; Scott M. Lowry

(57) ABSTRACT

The femoral stem prosthesis includes a prosthesis body having a neck, stem, and porous coating receiving area. A portion of a transition between the porous coating receiving area and the stem is defined by a recess where the porous coating receiving area inwardly extends by a depth relative to the stem while the porous coating receiving area is approximately flush with the stem about a remainder of the transition between the porous coating receiving area and the stem. A porous coating overlying the porous coating receiving area has a thickness approximately equal to the depth of the recess to define a smooth transition between the porous coating and the stem along the portion of the transition by the at least one recess and a collar outwardly extending relative to the stem by approximately the thickness along the remainder of the transition between the porous coating receiving area and the stem.

23 Claims, 11 Drawing Sheets

FEMORAL STEM WITH PARTIALLY RECESSED POROUS COATING

BACKGROUND OF THE INVENTION

The present invention relates generally to an improved femoral stem for use in hip joint arthroplasty. More specifically, the present invention relates to a femoral stem with a partially recessed porous coating that effectively forms a smooth arcuate transition at least between sections of the porous coating and the stem body to provide for smooth insertion of the femoral stem into a bone cavity during surgery, while maximizing press-fit engagement within the bone cavity.

In hip arthroplasty, a broach instrument is used to cut out a cavity in the proximal femur for seated reception of a femoral stem. Preferably, this cavity provides for at least some press-fit engagement of the porous coating of the femoral stem such that the bone surrounding the cavity is encouraged to grow into the porous coating over time. As a result, the femoral stem better locks into the cavity to secure the implant to the bone. To achieve this proximal press-fit engagement, femoral stems known in the art include a proximal porous coating that protrudes beyond the distal femoral stem body. In this respect, FIG. 1 illustrates a set of three such blade/Mueller type femoral stems 20, 20', 20" known in the prior art having an overhang or step 22, 22', 22" formed by application of a respective porous coating 24, 24', 24" to a respective portion of the stem body 26, 26', 26". FIG. 2 is an enlarged view of the prior art femoral stem 20 of FIG. 1, taken about the circle 2, and more specifically illustrates the outwardly protruding proximal porous coating 24 that creates the step 22 along the stem body 26. This ledge or step 22 is particularly undesirable on the medial side of the femoral stem 20 as it can cause the femoral stem 20 to hang up while being seated into the femoral bone cavity during surgery. If the femoral stem 20 does hang up during surgery, it may lead to difficulties seating the femoral stem 20, poor interdigitation of the bone with the porous coating 24, intraoperative and/or postoperative fracture, and/or poor fixation in the femoral cavity over the long-term.

Some femur stem designs known in the art attempt to rectify issues related to hang up by forming a recessed area around the entire perimeter of the femoral stem where the porous coating is applied. Example prior art devices are shown and described in U.S. Pat. Nos. 4,778,475; 5,013,324; 4,828,566; 4,608,055; 4,938,772, the contents of which are herein incorporated by reference in their entirety. The benefit of such a recessed area is that a porous coating having a certain thickness approximately equal to the depth of the recess can be applied to the stem body so the area of the porous coating is generally flush with the surrounding stem body, effectively eliminating the step. But, the drawback is that seated insertion of the femoral stem into the femoral cavity provides insufficient surface area contact of the porous coating with the bone because the porous coating is no longer outwardly extending. The Zimmer APS Natural-Hip System is another product currently available on the market that includes a recessed section on the stem body for receiving the porous coating. But, the Zimmmer APS Natural-Hip System only uses such a recessed area as a bone ingrowth surface, and not to facilitate insertion of the femur stem into the cavity of the femur. Thus, prior art devices either include the ledge or step 22, 22', 22" (thereby prone to hang up) and provide desired engagement between the porous coating and the bone, or the prior art femur stems have a recessed surface for reception of the porous coating, such as the Zimmer Natural Hip, and are undesirably incapable of press fitting the porous coating into the femur cavity to achieve desired engagement of the femur stem with the femur over the long term. Consequently, the prior art fails to disclose a recessed area or pocket along less than the entire perimeter of the femoral stem implant (e.g., only the medial side of the femoral stem implant), to eliminate the step, while maintaining substantial surface area engagement of the porous coating within the femur cavity.

To more specifically illustrate the abovementioned drawback, FIGS. 3-8 illustrate insertion of the prior art femoral stem 20 into a mockup of a femoral bone cavity 28 after broaching. More specifically, FIG. 3 illustrates initial insertion of the femoral stem 20 into the bone cavity 28. As shown in the enlarged view of FIG. 4, the stem body 26 easily fits into the enlarged upper end of the bone cavity 28 for slide-in reception. The hang up is not particularly problematic at this stage given that the step 22 is still well above an upper rim 30 of the bone cavity 28 formed from broaching. But, as the femoral stem 20 is continually inserted into the bone cavity 28, the medially outwardly projecting step 22 may have a tendency to catch on the upper rim 30, especially if the femoral stem 20 is inserted deeper into the bone cavity along its medial edge. In this respect, the surgeon must ensure that the femoral stem 20 is positioned somewhat away from the upper rim 30 so the medially outwardly projecting step 22 does not catch or hang up on this rim 30. If it does, the step 22 may catch, chip, fracture, or otherwise damage the bone of the upper rim 30, which can be particularly problematic when the femoral stem 20 is hammered into place. Moreover, required offsetting to clear the step 22 from the upper rim 30 may cause the femoral stem 20 to be misaligned when hammered into place, as previously mentioned above.

Even if the surgeon successfully clears the upper rim 30 without causing damage thereto, an undesirably low surface area of the porous coating 24 may abut or sit adjacent to the bone cavity 28. In this respect, FIG. 5 illustrates continued insertion of the femoral stem 20 into the bone cavity 28 as the stem body 28, and particularly as a distal tip 32, nears the bottom of the bone cavity 28. Here, the step 22 has already bypassed the upper rim 30, as better shown in FIG. 6. The femoral stem 20 is shown somewhat offset from the inner surface of the bone cavity 28, which provides for somewhat of a gap 34, as shown. When the femoral stem 20 is finally seated as shown in FIG. 7 and more specifically in the enlarged view of FIG. 8, the step 22 has a general single point of contact with the inner wall of the bone cavity 28, which forms the offset or gap 34 between the stem body 26 and the inner wall of the bone cavity 28. This gap 34 is particularly undesirable as it decreases the surface area contact of the porous coating 24 with the bone cavity 28 for purposes of ingrowth engagement after the formal stem 20 is implanted.

There exists, therefore, a significant need in the art for a femoral stem with a medially recessed porous coating limited only to the distal medial side of the coated area, which facilitates easier stem insertion by reducing the prior art step at the distal medial edge of the porous coating, while still allowing the femoral stem to simultaneously press-fit engage the entire porous coated surface to the femur cavity, except at the distal medial corner where there is no step. The present invention fulfills these needs and provides further related advantages.

SUMMARY OF THE INVENTION

The femoral stem prosthesis as disclosed herein may include a prosthesis body having a neck, a stem body, and a porous coating receiving area formed from the prosthesis body. A portion of a transition between the porous coating receiving area and the stem body may define at least one recess where the porous coating receiving area inwardly extends by a depth relative to the stem body while the porous coating receiving area is approximately flush with the stem body about a remainder of the transition between the porous coating receiving area and the stem body. In this respect, applying a porous coating over the porous coating receiving area by a thickness approximately equal to the depth of the recess defines a smooth transition between the porous coating and the stem body along the portion of the transition defined by the at least one recess. That is, the porous coating effectively fills the depth of the recess so the porous coating is flush with the stem body. Furthermore, the porous coating defines a collar outwardly extending relative to the stem body by approximately the thickness along the remainder of the transition between the porous coating receiving area and the stem body. The collar forms as a result of adding a layer of the porous coating to the area of the porous coating receiving area that is otherwise flush with the stem body.

In another aspect of this embodiment, the portion of the transition defined by the at least one recess may include a medial recess or a lateral recess. In this respect, there may be a smooth transitional geometry between the porous coating in the medial recess and a medially vertical section of the stem body leading toward a distal tip. The smooth transitional geometry may include a medially arcuate section that extends from the porous coating to the medially vertical section of the stem body. This facilitates implantation since the stem body can slide over an open rim of a bone cavity uninterrupted, i.e., starting at the distal tip of the stem body and over the medially vertical section of the stem body and the medially arcuate section at the transition between the stem body and porous coating. The smooth transitional geometry otherwise eliminates the lip that may catch on the open rim of the bone cavity during implantation.

In another embodiment, the at least one recess may include a pair of recesses that include a medial pocket formed in the porous coating and a lateral pocket formed in the porous coating opposite the medial pocket. Here, the femoral stem prosthesis may include a smooth medial transition along a medial arcuate section between the porous coating over the medial pocket and a medially vertical section of the stem body. The femoral stem prosthesis may further include a smooth lateral transition along a lateral arcuate section between the porous coating over the lateral pocket and a laterally vertical section of the stem body. As such, the femoral stem prosthesis may be of a size and shape for proximal press-fit engagement with the bone cavity substantially along the remainder of the transition, but not along the portion of the transition defined by the recesses/pockets.

Other features of the femoral stem prosthesis as disclosed herein may include a step between the porous coating and the neck along a medial arc. In this respect, the porous coating may extend outwardly a distance approximately the thickness of the porous coating and about the femoral stem prosthesis adjacent the neck. Also, the remainder of the transition between the porous coating and the stem body may include a collar that has a U-shape and generally encompasses an anterior, a posterior, and a lateral side of the femoral stem prosthesis. Alternatively, the at least one recess may include a recess that wraps around at least a portion of the medial, the anterior, the posterior, and/or the lateral sides of the femoral stem prosthesis.

In another embodiment as disclosed herein, the femoral stem prosthesis may include a prosthesis body having a neck and a stem body generally opposite the neck. A porous coating receiving area formed from the prosthesis body may be configured to at least partially selectively receive and retain a porous coating thereon. Furthermore, the femoral stem prosthesis may include a medially arcuate section of the porous coating adjacent a medially vertical section of the stem body. A smooth medial transition between the medially arcuate section of the porous coating and the medially vertical section of the stem body may include at least one recess formed in the porous coating receiving area that extends inwardly by a depth relative to the stem body such that applying the porous coating over the porous coating receiving area by a thickness approximately equal to the depth of the recess results in the porous coating along the medially arcuate section being substantially flush with the medially vertical section of the stem body.

Additionally, a collar of the porous coating may extend outwardly relative to the stem body by approximately the thickness along a portion of the porous coating receiving area adjacent to and approximately flush with the stem body. The collar may be formed substantially along an anterior, a posterior, and a lateral side of the femoral stem and include a U-shape. As such, the femoral prosthesis may have a size and shape for proximal press-fit engagement with a bone cavity substantially along the collar, but not along the smooth medial transition between the medially arcuate section of the porous coating and the medially vertical section of the stem body. Accordingly, the smooth medial transition of the femoral stem prosthesis permits continuous and uninterrupted sliding along the medially arcuate section of the porous coating and the medially vertical section of the stem body over an open rim of the bone cavity during implantation.

Other features of this embodiment may include a lateral pocket formed in the porous coating receiving area opposite the at least one recess, a smooth lateral transition along a lateral arcuate section between the porous coating over the lateral pocket and a laterally vertical section of the femoral stem, and a medial step between the porous coating and the neck. Moreover, the porous coating may extend outwardly by the thickness of the porous coating about an anterior, a posterior, a lateral, and a medial sides of the prosthesis body adjacent the neck.

In another aspect of the embodiments disclosed herein, an alternative femoral stem prosthesis may include a prosthesis body having a neck extending from one side thereof and a stem extending from another side thereof generally opposite the neck and terminating at a distal tip. Moreover, the prosthesis body may include a porous coating receiving area formed therein. Additionally, a medial step along a medial arc of the prosthesis body may define a medial transition wherein the stem projects out and away from the porous coating receiving area. Similarly, a lateral step along a lateral arc of the prosthesis body opposite the medial arc may define a lateral transition wherein the stem projects out and away from the porous coating receiving area. As such, a porous coating may be selectively applied to the porous coating receiving area in an amount so the porous coating is flush with the stem along the medial arc and the lateral arc and extends outwardly along the anterior and posterior sides of the femoral stem prosthesis. Accordingly, the medial arc and the lateral arc of the femoral stem prosthesis may slide in uninterrupted relation over an open rim of a bone cavity during implantation while the femoral stem prosthesis is of a size and shape for proximal press-fit engagement within the bone cavity along the anterior and the posterior sides by way of engagement with the porous coating. The femoral stem prosthesis may also include an upper step between the porous coating and the neck along the medial arc, wherein the porous coating extends outwardly about the anterior, the posterior, a lateral, and a medial sides of the prosthesis body adjacent the neck.

Additionally, in other embodiments, the femoral stem prosthesis may include a medially recessed porous coating generally including a femur body including a taper, neck, porous coating receiving region, and stem body having a distal tip opposite the taper. The porous coating receiving region may include a medial recess or pocket that forms a ledge or shoulder between the receiving region and the lower stem body prior to coating the receiving region with the porous coating. The anterior, posterior, and lateral sides of the receiving region may be flush with the lower stem body. Thereafter, a porous coating having a predetermined thickness that may be approximately equal to the depth of the ledge or shoulder formed by the recess or pocket between the receiving region and the lower stem body may be applied to the receiving region. The resulting structure of the femoral stem provides for a smooth, flush, or otherwise co-planar arced medial transition between the receiving region with the porous coating thereon and the lower stem body. The anterior, posterior, and lateral sides of the receiving region with the porous coating thereon generally extend or protrude outwardly, thereby forming a U-shaped shoulder relative to the lower stem body. As a result, the femoral stem with a medially recessed porous coating effectively forms a smooth arcuate transition at least between medial sections of the porous coating and the stem body to provide for smooth insertion of the femoral stem into a bone cavity during surgery.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
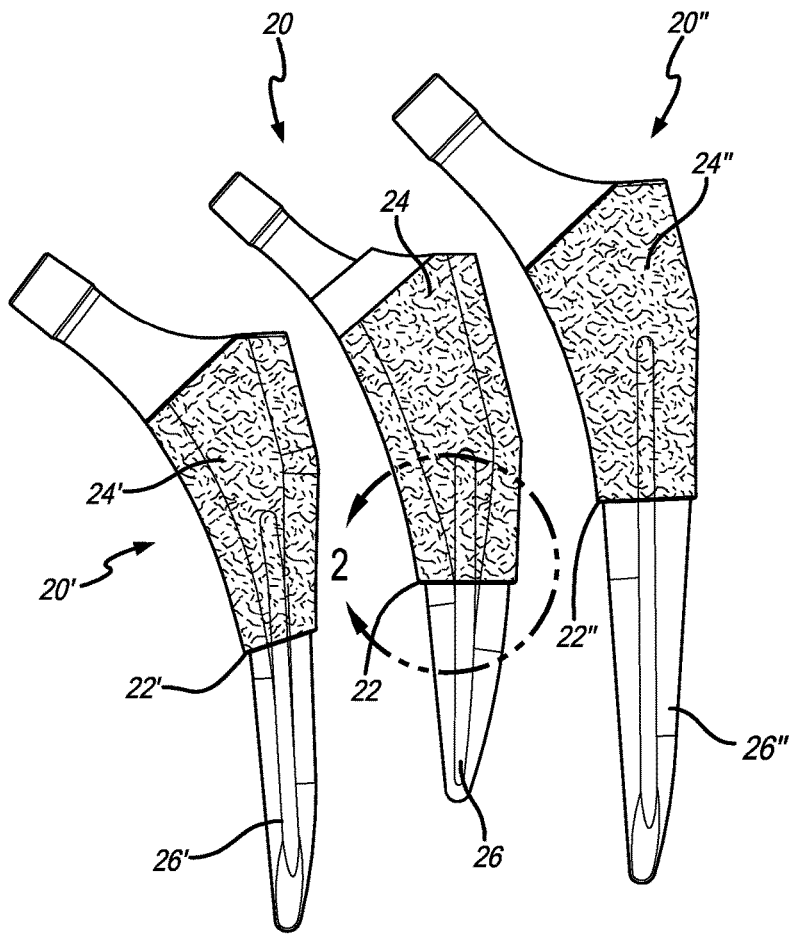
FIG. 1 is a general perspective view of three prior art femur stems including a porous coating with a medial step.
Figure 2:
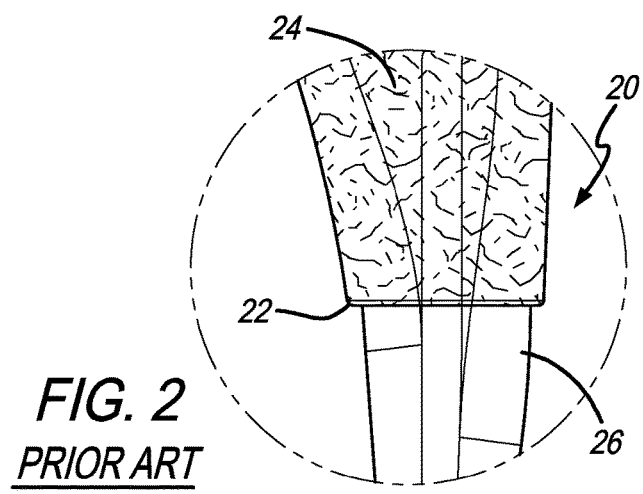
FIG. 2 is an enlarged view taken generally about the circle 2 of FIG. 1, further illustrating the medial step of one of the prior art femur stems.
Figure 3:
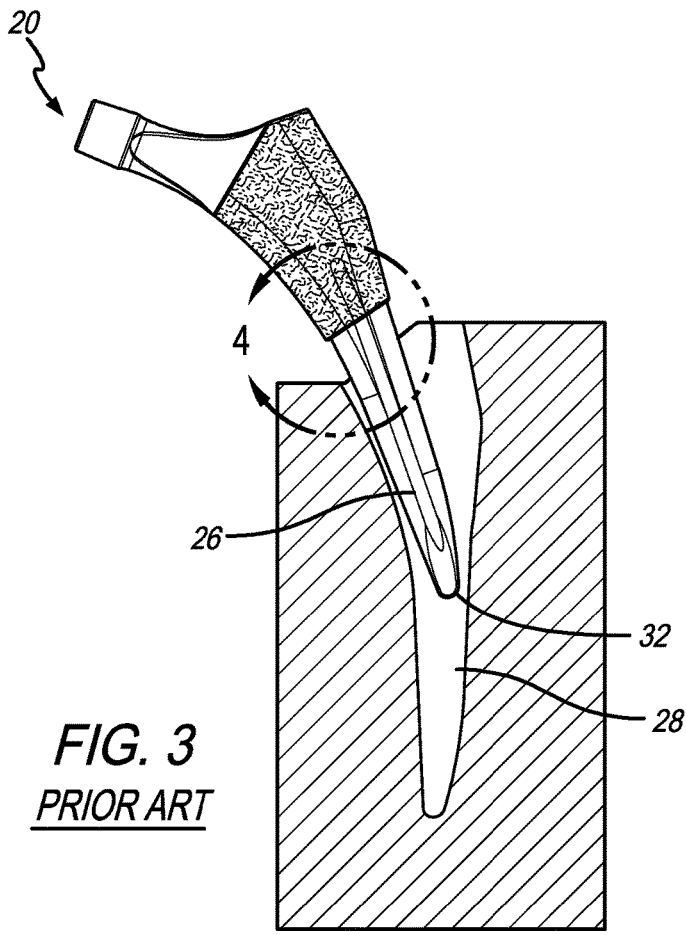
FIG. 3 is a perspective view of the prior art femur stem of FIG. 1, illustrating initial insertion into a bone cavity.
Figure 4:
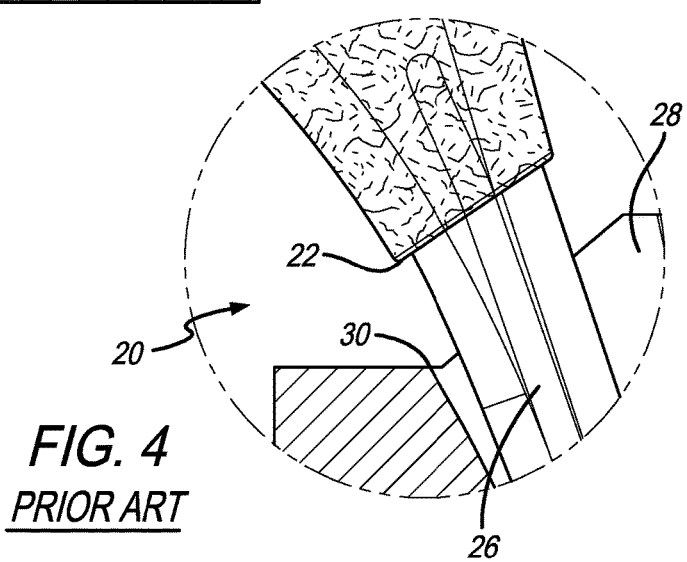
FIG. 4 is an enlarged perspective view taken about the circle 4 in FIG. 3, more specifically illustrating orientation of the step relative to an upper rim of the bone cavity.
Figure 5:
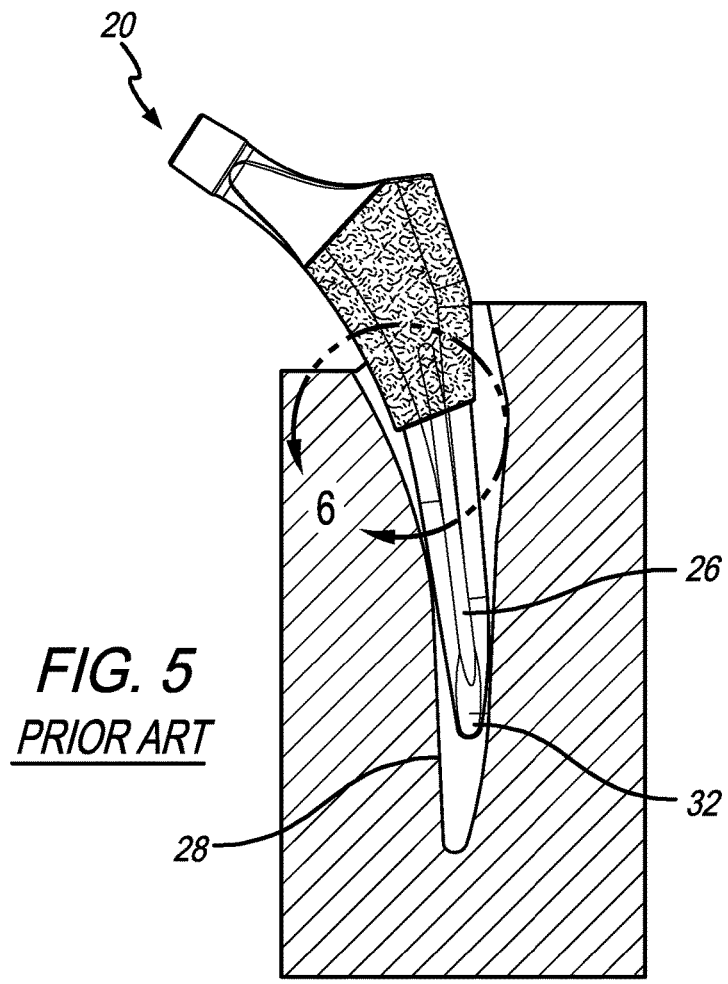
FIG. 5 is a perspective view similar to FIG. 3, illustrating further insertion of the prior art femur stem into the bone cavity.
Figure 6:
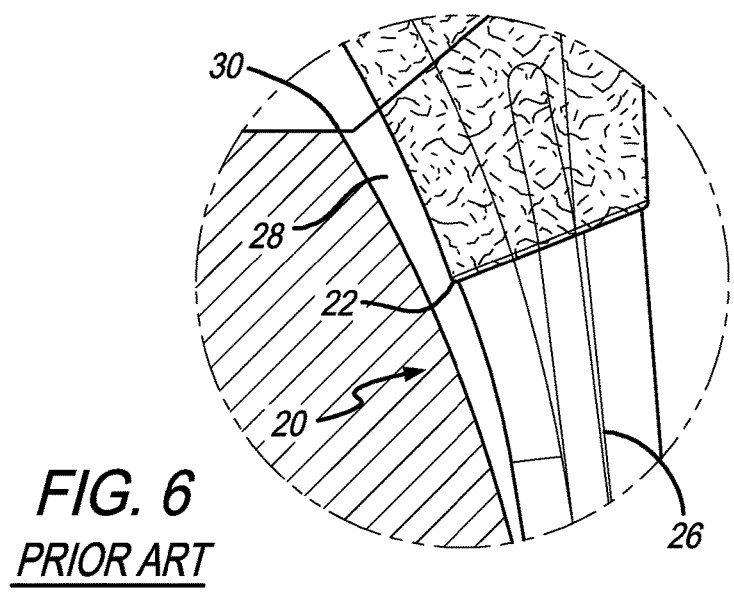
FIG. 6 is an enlarged perspective view taken about the circle 6 in FIG. 5, more specifically illustrating orientation of the step relative to the bone cavity during further insertion of the prior art femoral stem into the bone cavity.
Figure 7:
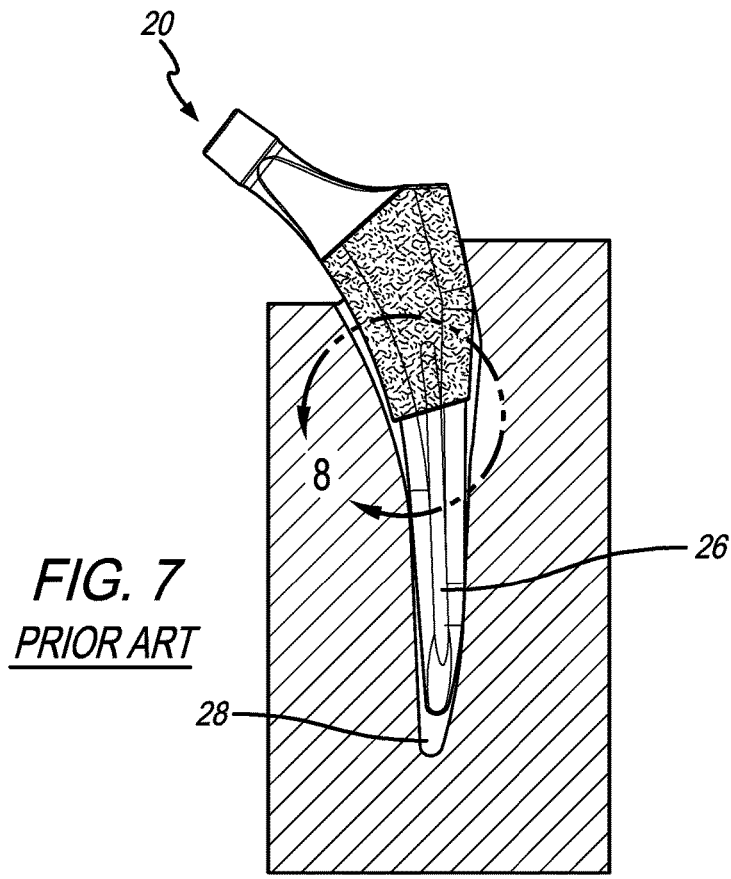
FIG. 7 is a perspective view similar to FIG. 3, illustrating final insertion of the prior art femur stem into the bone cavity.

As shown in the exemplary drawings, a femoral stem with medially recessed porous coating is referred to generally in FIGS. 9-18 by reference numeral 36. As discussed in detail below, in one embodiment, the femoral stem 36 creates a smooth transition between the distal stem body and the proximal porous coated area to allow the femoral stem 36 to more easily and fully seat into the femur bone cavity during hip arthroplasty procedures. Additionally, because the porous coating is left extended on all surfaces but the medial curve, the femur stem 36 still achieves proximal press-fit engagement with the bone cavity when implanted. In other words, the femoral stem 36 may seat fully within the bone cavity 28 without hanging on the upper rim 30 of the bone cavity 28 during insertion, while maintaining sufficient press-fit engagement between the bone of the cavity 28 and the porous coating.

Figure 9:
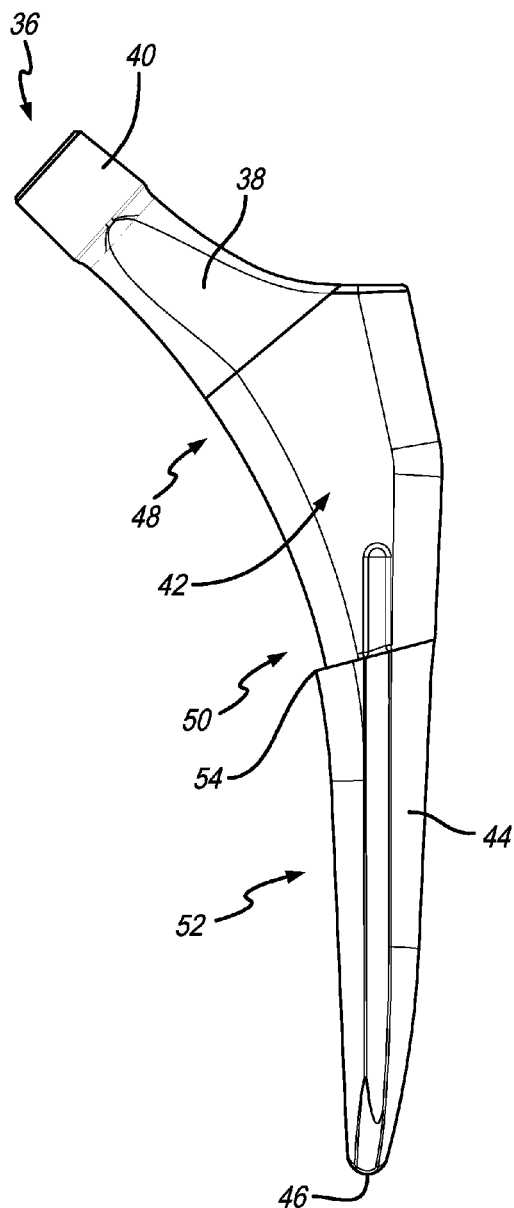
FIG. 9 is a perspective view of one embodiment of a femoral stem with medially recessed porous coating as disclosed herein, illustrating a medial recess before application of the porous coating.

More specifically, FIG. 9 illustrates the femoral stem 36 in an uncoated state. In general, the femoral stem 36 is shown in FIG. 9 including a neck 38 having a head connector 40 at one end, and a porous coating receiving region 42 formed between the neck 38 and a stem body 44 terminating at a distal tip 46 at an opposite end. The medial curvature of the femoral stem 36 generally indicated by the arrow 48 in FIG. 9 transitioning between the neck 38 and the receiving region 42 is preferably smooth or flush along the arc, as shown. But, the transition between the receiving region 42 and the stem body 44 is different. In this respect, the receiving region 42 includes a medially arcuate section 50 terminating in a medially recessed position or pocket relative to a generally medially vertical section 52 of the stem body 44, thereby forming a ledge or shoulder 54 therebetween. During manufacture of the femoral stem 36, and before adding a porous coating 56, this medially recessed position or pocket of the medially arcuate section 50 may be formed by machining, forging, additive manufacturing or casting. The depth of this recess or pocket is designed to match the thickness of the porous coating 56 such that the transition between the proximal porous coating 56 and the distal stem body 44 is smooth on the medial side, as shown best in FIGS. 10, 12, 14, 16 and 18.

Before coating, the recess or pocket generally forms the ledge or shoulder 54 between the transition of the medially arcuate section 50 of the receiving region 42 and the medially vertical section 52 of the stem body 44, but only along the medial part of the femur stem 36. The depth of the ledge or shoulder 54 may vary as needed and/or desired, depending on the application. The anterior, posterior and lateral surfaces of the receiving region 42 and the stem body 44 are flush or smooth in the configuration shown in FIG. 9. Of course, such a recess or pocket could wrap around a portion or the entire anterior, posterior, and/or lateral sides of the femoral stem 36 such that the ledge or shoulder 54 extends partially or all away around each of anterior, posterior, and/or lateral sides of the femoral stem 36.

Figure 10:
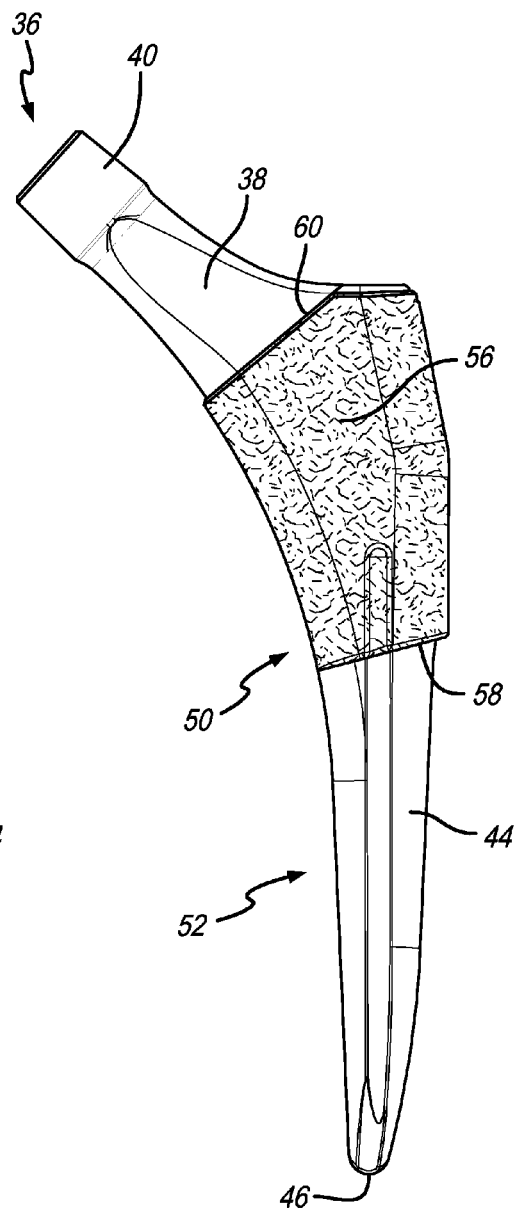
FIG. 10 is a perspective view of the femoral stem of FIG. 9, further illustrating the femoral stem having the medially recessed porous coating applied.

FIG. 10 illustrates the femoral stem 36 in a coated state wherein a layer of the porous coating 56 (similar to porous coating 24 described above) is applied to the receiving region 42. The thickness of the porous coating 56 may vary depending on the femoral stem 36, but it is preferably approximately equal to the depth of the ledge or shoulder 54 so that final finishing results in a smooth transitional geometry between the medially vertical section 52 of the stem body 44 and the porous coating 56 applied along the medially arcuate section 50 (FIG. 9). As such, in the configuration shown in FIG. 10, the medially arcuate section 50 of the femoral stem 36 is now generally smooth or flush with the medially vertical section 52 of the stem body 44, thereby effectively eliminating the ledge or shoulder 54 therebetween. Although, the addition of the porous coating 36 of predetermined thickness effectively increases the thickness such that the anterior, posterior, and/or lateral sides of the porous coating 56 extend outwardly relative to the anterior, posterior and/or lateral sides of the stem body 44, thereby creating a three-sided or U-shaped outwardly protruding shoulder 58 that better maximizes surface area contact of the porous coating 56 with the bone when the femoral stem 36 is implanted. The addition of the porous coating 56 of predetermined thickness also increases the thickness thereof such that the anterior, posterior, lateral, and/or medial sides of the porous coating 56 extend outwardly relative to the anterior, posterior, lateral, and/or medial sides of the neck 38, thereby creating a four-sided or ring-shaped outwardly protruding shoulder 60. Of course, the porous coating 56 could vary in thickness and extent depending on the desired roughness.

Figures 11, 12:
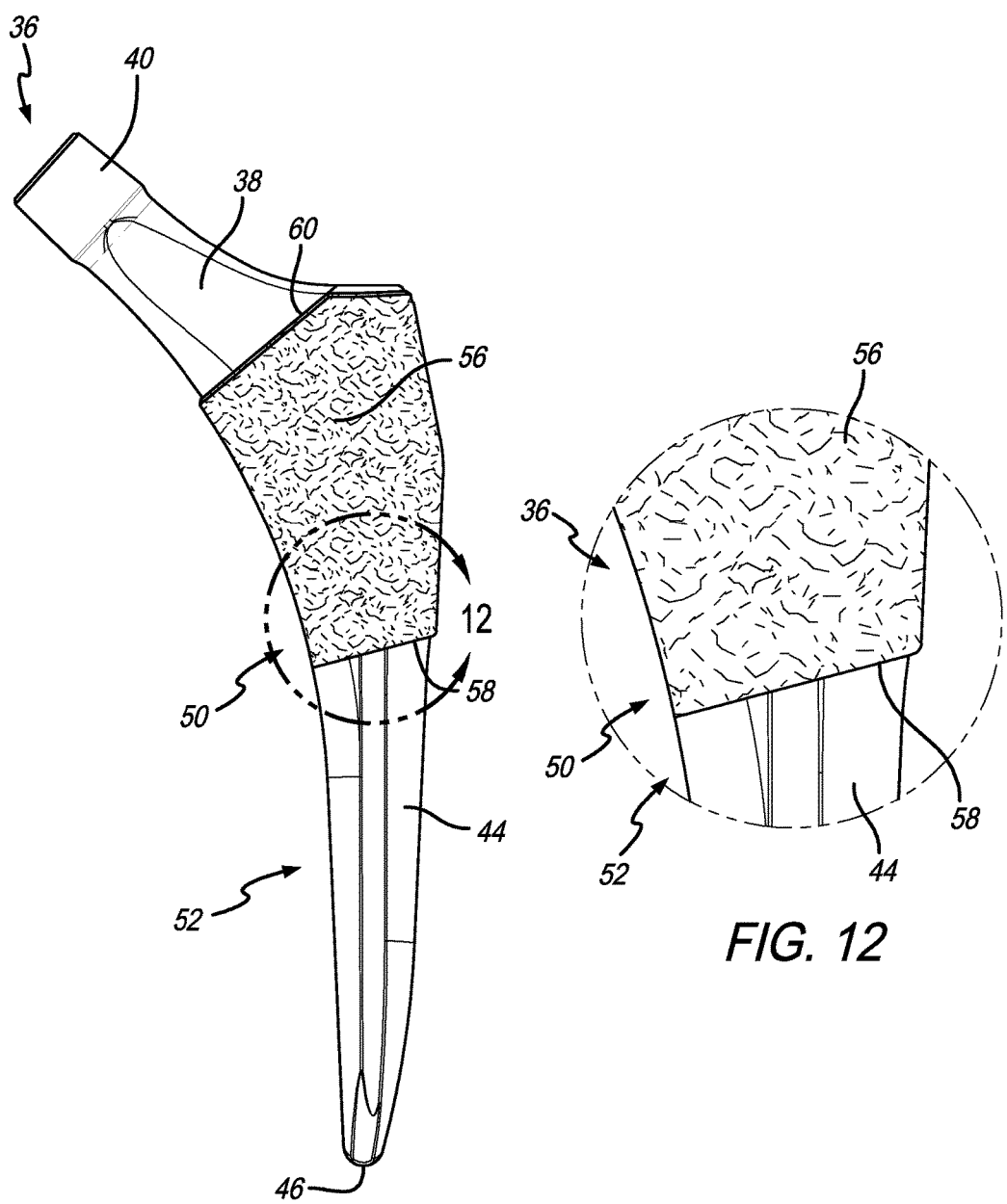
FIG. 11 is a left side elevation view further illustrating the femoral stem of FIG. 10 with the medially recessed porous coating.
FIG. 12 is an enlarged left side elevation view taken about the circle 12 in FIG. 11, further illustrating flush medial alignment of the porous coating with the stem body, and the porous coating in stepped anterior relation.

FIGS. 11 and 12 more specifically illustrate the femoral stem 36 having a smooth or flush transition between the medially vertical section 52 of the stem body 44 and the medially arcuate section 50 of the porous coating 56. Note that there is a protruding or outwardly extending edge (i.e., the U-shaped shoulder 58) of the porous coating 56 on all faces (i.e., anterior, posterior and lateral sides). This configuration, as shown in more detail below with respect to FIGS. 13-18, provides for enhanced slide-in engagement into the corresponding bone cavity without any issues related to hang-up, as described above, while simultaneously providing enhanced initial press-fit engagement and fixation with increased interdigitation of bone with the porous coating 56 over time. That is, the geometry of the femur stem 36 allows it to more consistently seat along the entire medial curvature (e.g., as denoted by the arrow 48, the medially arcuate section 50, and, at least initially, along the medially vertical section 52), without digging in or catching on the upper rim 30 of the bone cavity 28 because the arcuate surfaces provide for a continuous and smooth arcuate transition between the porous coating 56 and the stem body 44 along the generally curved medial edge. Because the porous coating 56 still extends outwardly beyond the respective anterior, posterior, and/or lateral surfaces of the stem body 44, thereby forming the U-shaped shoulder 58, the femoral stem still attains sufficient press-fit engagement with the bone cavity 28.

Figure 13:
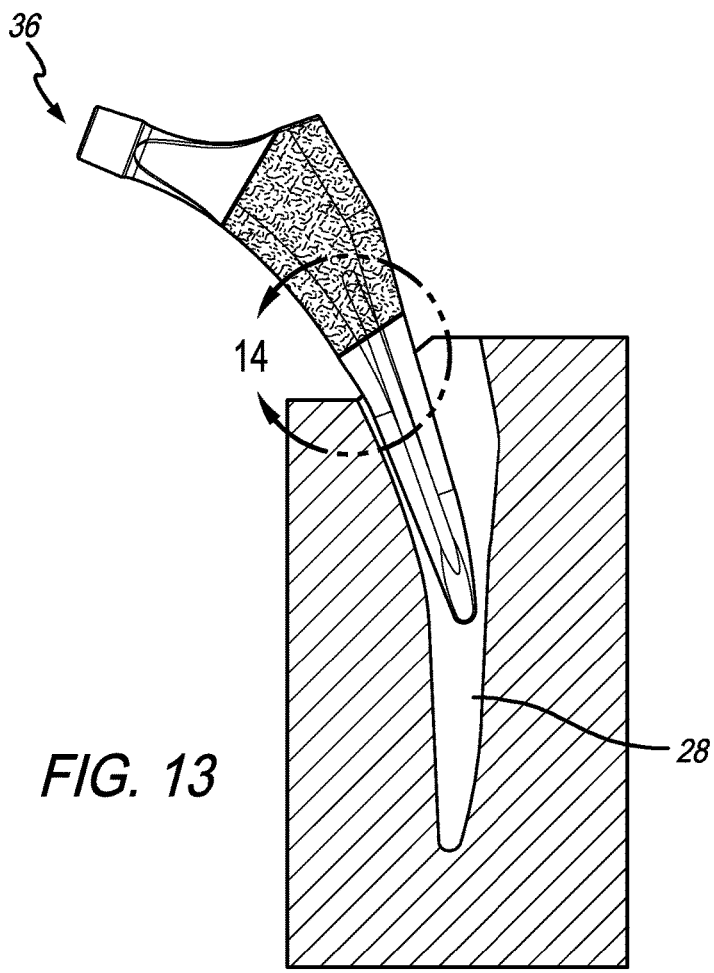
FIG. 13 is a perspective view of the femoral stem of FIGS. 10-12, illustrating initial insertion into a bone cavity.
Figure 14:
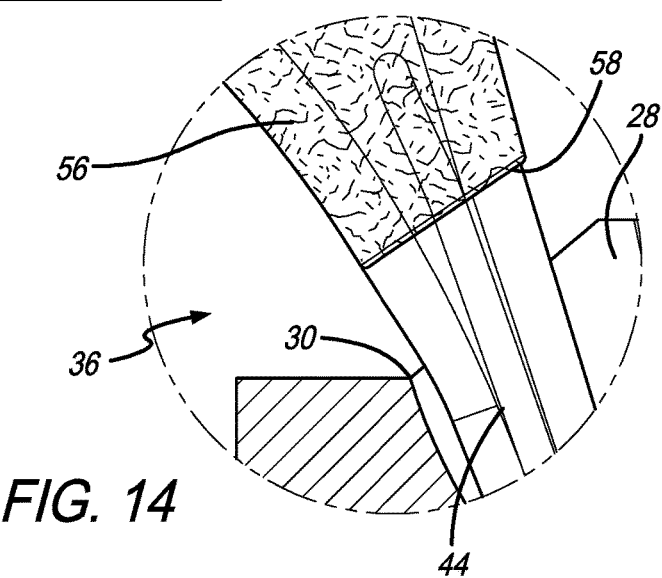
FIG. 14 is an enlarged perspective view taken about the circle 14 in FIG. 13, further illustrating initial insertion of the femoral stem of FIGS. 10-12 into the bone cavity.

To illustrate the advantages of the femoral stem 36 disclosed herein, and compared to the prior art femoral stem 20 discussed above with respect to FIGS. 1-8, FIGS. 13-18 more specifically illustrate insertion of the femoral stem 36 into a mockup of the femoral bone cavity 28 after broaching. In this respect, FIG. 13 illustrates initial insertion of the femoral stem 36 into the bone cavity 28. As shown in the enlarged view of FIG. 14, the stem body 44 similarly easily fits into the enlarged upper end of the bone cavity 28 for slide-in reception. As the femoral stem 36 is continually inserted into the bone cavity 28, the medial side of the femoral stem 36 may have a tendency to slide near or relative to (e.g., along) the upper rim 30. As discussed above, this was problematic for the prior art femoral stem 20 because the outwardly projecting step 22 may have a tendency to catch on the upper rim 30 as the femoral stem 20 is inserted deeper into the bone cavity 28. But, in the case of the femoral stem 36 disclosed herein, the step 22 is largely eliminated by including a recessed receiving region 42 along the medial side of the femoral stem 36. In turn, the medially arcuate section 50 and the medially vertical section 52 include a smooth transition between the two, thereby effectively eliminating the step 22. The surgeon no longer needs to ensure that the femoral stem 36 clears the upper rim 30. Rather, the surgeon can simply slide the femoral stem 36 medially and along the upper rim 30 without worrying that the femoral stem 36 will catch or hang up on the rim 30. This provides for enhanced alignment of the femoral stem 36 within the bone cavity 28 during surgery.

Figure 8:
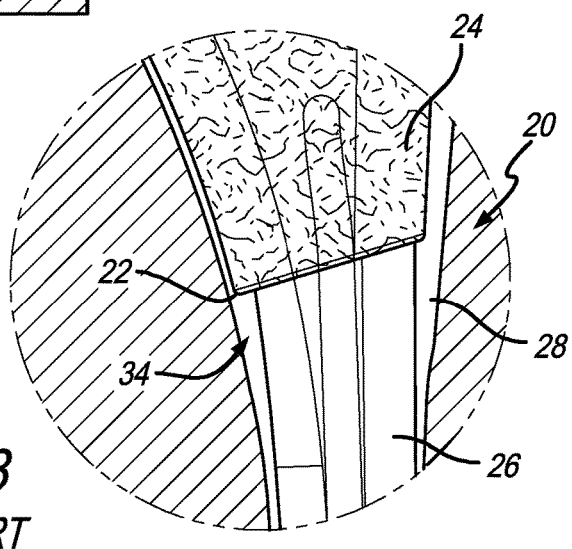
FIG. 8 is an enlarged perspective view taken about the circle 8 in FIG. 7, more specifically illustrating final insertion of the prior art femoral stem into the bone cavity and the gap therebetween.
Figure 15:
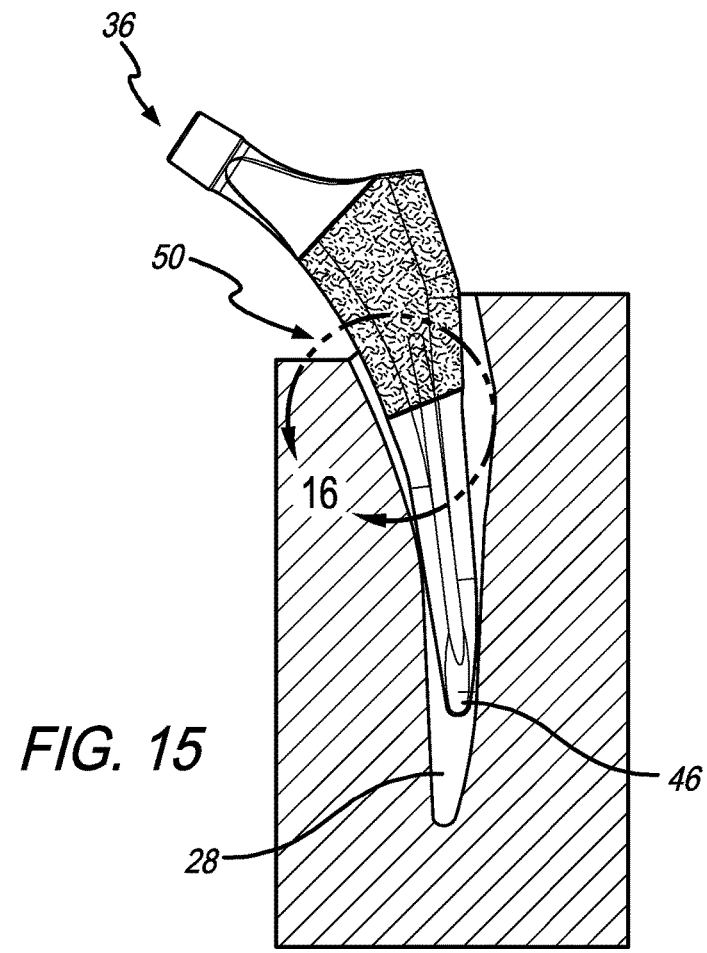
FIG. 15 is a perspective view similar to FIG. 13, illustrating further insertion of the femoral stem of FIGS. 10-12 into the bone cavity.
Figure 16:
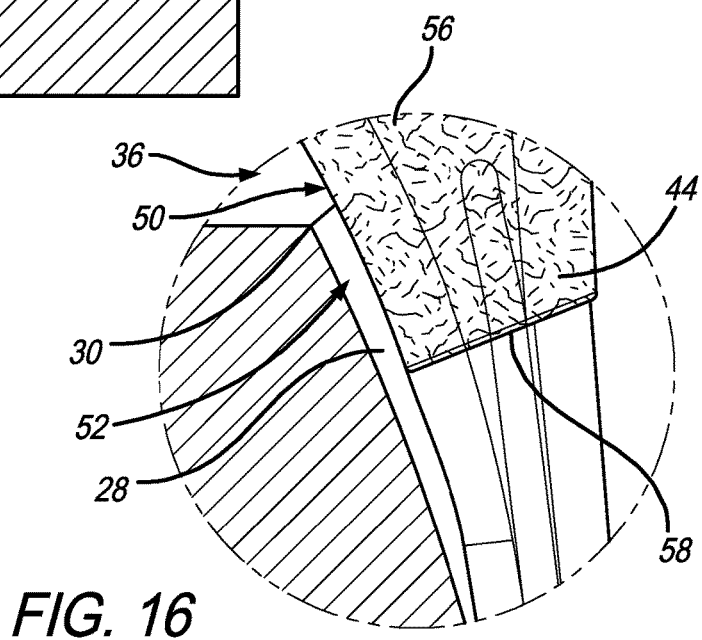
FIG. 16 is an enlarged perspective view taken about the circle 16 in FIG. 15, further illustrating flush slide-in insertion of the femoral stem of FIGS. 10-12 relative to the upper rim of the bone cavity.
Figure 17:
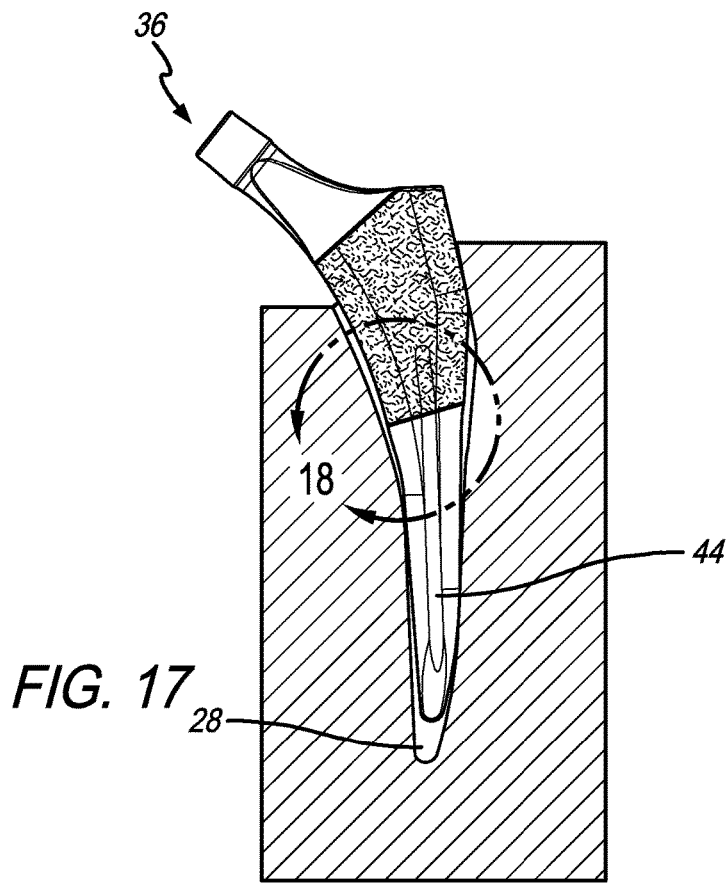
FIG. 17 is a perspective view similar to FIG. 13, illustrating final insertion of the femoral stem into the bone cavity.
Figure 18:
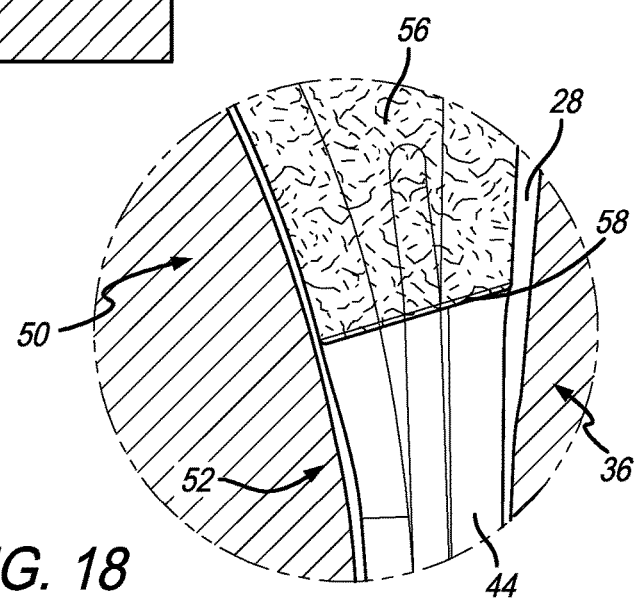
FIG. 18 is an enlarged perspective view taken generally about the circle 18 in FIG. 17, further illustrating flush medial mounting of the femoral stem of FIGS. 10-12 within the bone cavity.

FIG. 15 further illustrates continued insertion of the femoral stem 36 into the bone cavity 28 as the stem body 44, and particularly the distal tip 46 nears the bottom of the bone cavity 28. Here, as shown in the enlarged view of FIG. 16, the benefit of the smooth transition between the medially arcuate section 50 and the medially vertical section 52 can be shown moving past the upper rim 30 without interference. The femoral stem 36 is shown still being somewhat offset from the inner surface of the bone cavity 28, before the femoral stem 36 is completely (snugly) inserted into the bone cavity 28. When the femoral stem 36 is finally seated as shown in FIG. 17, and more specifically in the enlarged view of FIG. 18, the smooth transition between the medially arcuate section 50 and the medially vertical section 52 provides for adjacent seated reception of the medial side of the femoral stem 36 against the bone cavity 28. This may increase the surface area contact between the medial side of the femoral stem 36 with the bone cavity 28, as opposed to the general single point of contact (and the gap 34) with the inner wall of the bone cavity 28, as described above with respect to the prior art femoral stem 20. Accordingly, the femoral stem 36 as disclosed herein is able to effectively eliminate the undesirable gap 34 (FIG. 8). Moreover, the U-shaped shoulder 58 still permits substantial engagement of the porous coating 56 with the surrounding bone cavity 28. Depending on the geometry of this recess or pocket forming the ledge/shoulder 54, the amount of press-fit engagement may be changed by increasing or decreasing the transition between the medially arcuate section 50 and the medially vertical section 52, prior to addition of the porous coating 56. Such modifications may respectively create snugger or looser feeling stems, based on surgeon preference and implant geometry. Alternatively, the femoral stem 36 may include comparable geometry with an oversized distal end, which steps down to the proximal porous coating 56. Such a femur stem 36 could have essentially the same geometry without the pocket, per se.

Figure 19:
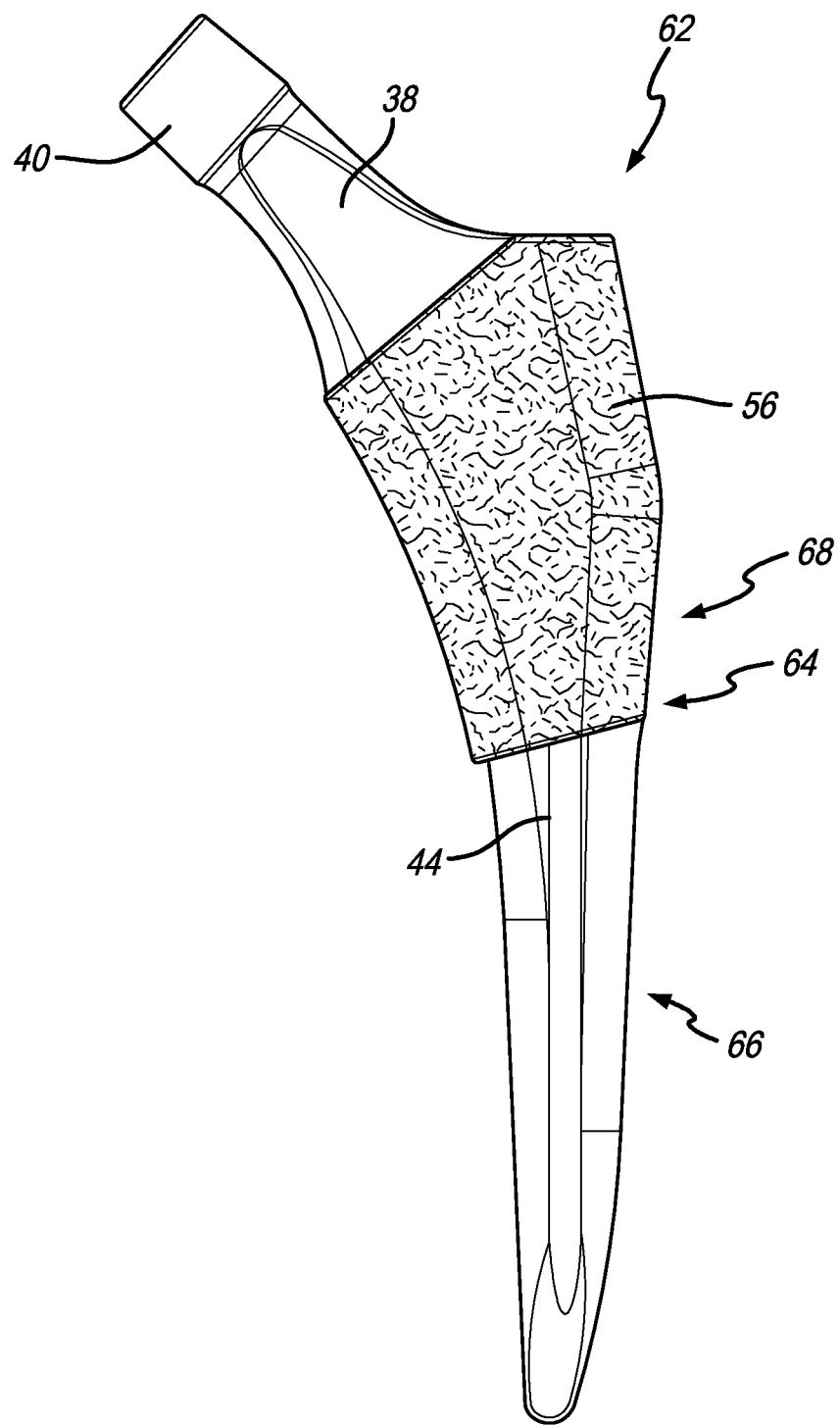
FIG. 19 is a perspective view of an alternative embodiment of a femoral stem including a laterally recessed porous coating.
Figure 20:
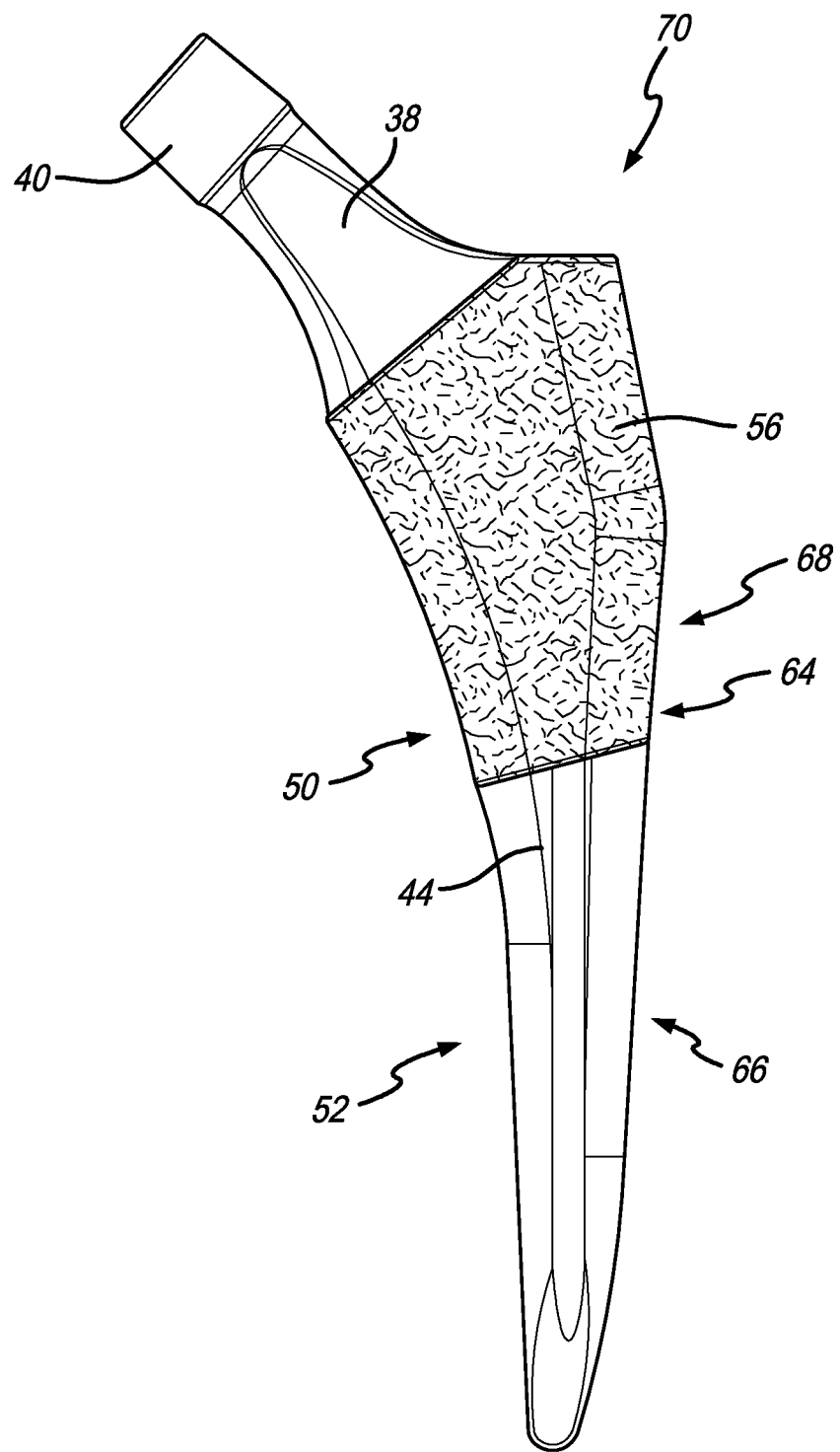
FIG. 20 is a perspective view of another embodiment of a femoral stem as disclosed herein, including a medially and laterally recessed porous coating.

FIGS. 19 and 20 illustrate alternatives to the femoral stem with medially recessed porous coating 36. In this respect, FIG. 19 discloses a femoral stem with laterally recessed porous coating 62. In this embodiment, the femoral stem 62 creates a smooth transition laterally between the distal stem body and the proximal porous coated area to allow the femoral stem 62 to more easily and fully seat into the femur bone cavity during hip arthroplasty procedures. Additionally, because the porous coating is left extended on all surfaces but the lateral curve, the femur stem 62 may still achieve proximal press-fit engagement with the bone cavity when implanted. In other words, the femoral stem 62 may seat fully within the bone cavity 28 without laterally hanging on the upper rim 30 of the bone cavity 28 during insertion, while maintaining sufficient press-fit engagement between the bone of the cavity 28 and the porous coating.

In general, the femoral stem 62 is shown in FIG. 19 including the neck 38 having the head connector 40 at one end, and the porous coating 56 between the neck 38 and the stem body 44. Similar to the above, the femoral stem 62 may include a recess or pocket near arrow 64 so that, when the porous coating 56 is applied to the above-mentioned receiving region 42, the layer of the porous coating 56 preferably approximately equals the depth of the ledge or shoulder so the final finishing results in a smooth (or smoother) transitional geometry between a laterally vertical section 66 of the stem body 44 and the porous coating 56 applied along a lateral section 68. As such, in the configuration shown in FIG. 19, the lateral section 68 of the femoral stem 62 is now generally smooth or flush with the laterally vertical section 66 of the stem body 44, thereby effectively eliminating any ledge or shoulder therebetween, as described herein.

FIG. 20 illustrates another alternative embodiment of a femoral stem with medially and laterally recessed porous coating 70. Here, the femoral stem 70 illustrated in FIG. 20 is basically a combination of the femoral stems 36 and 62, namely before application of the porous coating 56, the receiving region 42 includes a medial and lateral recess or pocket, thereby forming both a medial and lateral ledge. When the porous coating 56 having a predetermined thickness preferably approximately the thickness of the depth of the ledges, this creates a smooth transition between the medially arcuate section 50 and the medially vertical section 52, on the medial side of the femoral stem 70, while also creating a smooth transition between the laterally vertical section 66 and the lateral section 68 on the lateral side of the femoral stem 70.

Of course, the principles of FIGS. 19 and 20 could be extended to other surfaces. That is, the smooth transition between the porous coating 56 and the stem body 44 could be on one or more sides of the femoral stem (e.g., the medial, lateral, anterior, and/or posterior sides). Of course, in other embodiments, the smooth transition may be between just one side, two sides, three sides, or all four sides, as discussed herein.

Although several embodiments have been described in detail for purposes of illustration, various modifications may be made without departing from the scope and spirit of the invention. Accordingly, the invention is not to be limited, except as by the appended claims.

What is claimed is:

1. A femoral stem prosthesis, comprising:
 a prosthesis body having a neck and a stem body;
 a porous coating receiving area formed from the prosthesis body;
 a portion of a transition between the porous coating receiving area and the stem body defined by at least one recess where the porous coating receiving area inwardly extends by a depth relative to the stem body while the porous coating receiving area is approximately flush with the stem body about a remainder of the transition between the porous coating receiving area and the stem body; and
 a porous coating overlying the porous coating receiving area and having a thickness approximately equal to the depth of the recess to define a smooth transition between the porous coating and the stem body along the portion of the transition defined by the at least one recess and to define a collar outwardly extending relative to the stem body by approximately the thickness along the remainder of the transition between the porous coating receiving area and the stem body.

2. The femoral stem prosthesis of claim 1, wherein the portion of the transition defined by the at least one recess comprises a medial recess or a lateral recess.

3. The femoral stem prosthesis of claim 2, including a smooth transitional geometry between the porous coating in the medial recess and a medially vertical section of the stem body leading toward a distal tip.

4. The femoral stem prosthesis of claim 3, wherein the smooth transitional geometry comprises a medially arcuate section extending from the porous coating to the medially vertical section of the stem body.

5. The femoral stem prosthesis of claim 4, wherein the smooth transitional geometry along the medially arcuate section permits uninterrupted sliding of the medially arcuate section over an open rim of a bone cavity during implantation.

6. The femoral stem prosthesis of claim 1, wherein the at least one recess comprises a pair of recesses including a medial pocket formed in the porous coating receiving area and a lateral pocket formed in the porous coating receiving area opposite the medial pocket.

7. The femoral stem prosthesis of claim 6, including a smooth medial transition along a medial arcuate section between the porous coating over the medial pocket and a medially vertical section of the stem body and a smooth lateral transition along a lateral arcuate section between the porous coating over the lateral pocket and a laterally vertical section of the stem body.

8. The femoral stem prosthesis of claim 1, wherein the femoral stem prosthesis comprises a size and shape for proximal press-fit engagement with a bone cavity substantially along the remainder of the transition, but not along the portion of the transition defined by the at least one recess.

9. The femoral stem prosthesis of claim 1, including a step between the porous coating and the neck along a medial arc.

10. The femoral stem prosthesis of claim 1, wherein the remainder of the transition comprises an anterior, a posterior, and a lateral side of the femoral stem prosthesis.

11. The femoral stem prosthesis of claim 10, wherein the at least one recess comprises a recess wrapping around at least a portion of the medial, the anterior, the posterior, and/or the lateral sides of the femoral stem prosthesis.

12. The femoral stem prosthesis of claim 1, wherein the collar comprises a U-shaped collar.

13. The femoral stem prosthesis of claim 1, wherein the porous coating extends outwardly by the thickness about the femoral stem prosthesis adjacent the neck.

14. A femoral stem prosthesis, comprising:
a prosthesis body having a neck and a stem body generally opposite the neck;
a porous coating receiving area formed from the prosthesis body and configured to at least partially selectively receive and retain a porous coating thereon;
a medially arcuate section of the porous coating adjacent a medially vertical section of the stem body;
a smooth medial transition between the medially arcuate section of the porous coating and the medially vertical section of the stem body, the smooth medial transition comprising at least one recess formed in the porous coating receiving area extending inwardly by a depth relative to the stem body such that applying the porous coating over the porous coating receiving area by a thickness approximately equal to the depth of the recess results in the porous coating along the medially arcuate section being substantially flush with the medially vertical section of the stem body; and
a collar of the porous coating outwardly extending relative to the stem body by approximately the thickness along a portion of the porous coating receiving area adjacent to and approximately flush with the stem body, wherein the femoral prosthesis has a size and shape for proximal press-fit engagement with a bone cavity substantially along the collar, but not along the smooth medial transition between the medially arcuate section of the porous coating and the medially vertical section of the stem body.

15. The femoral stem prosthesis of claim 14, wherein the smooth medial transition permits continuous and uninterrupted sliding along the medially arcuate section of the porous coating and the medially vertical section of the stem body over an open rim of the bone cavity during implantation.

16. The femoral stem prosthesis of claim 14, including a lateral pocket formed in the porous coating receiving area opposite the at least one recess.

17. The femoral stem prosthesis of claim 16, including a smooth lateral transition along a lateral arcuate section between the porous coating over the lateral pocket and a laterally vertical section of the femoral stem.

18. The femoral stem prosthesis of claim 14, including a medial step between the porous coating and the neck.

19. The femoral stem prosthesis of claim 14, wherein the collar is formed substantially along an anterior, a posterior, and a lateral side of the femoral stem and comprises a U-shape.

20. The femoral stem prosthesis of claim 14, wherein the porous coating extends outwardly by the thickness about an anterior, a posterior, a lateral, and a medial sides of the prosthesis body adjacent the neck.

21. A femoral stem prosthesis, comprising:
a prosthesis body having a neck extending from one side thereof and a stem extending from another side thereof generally opposite the neck and terminating at a distal tip;
a porous coating receiving area formed from the prosthesis body;
a medial step along a medial arc of the prosthesis body defining a medial transition wherein the stem projects out and away from the porous coating receiving area;
a lateral step along a lateral arc of the prosthesis body opposite the medial arc and defining a lateral transition wherein the stem projects out and away from the porous coating receiving area; and
a porous coating selectively applied to the porous coating receiving area in an amount so the porous coating is flush with the stem along the medial arc and the lateral arc and extends outwardly along an anterior and a posterior sides of the femoral stem prosthesis, wherein the medial arc and the lateral arc of the femoral stem prosthesis slide in uninterrupted relation over an open rim of a bone cavity during implantation while the femoral stem prosthesis is of a size and shape for proximal press-fit engagement within the bone cavity along the anterior and the posterior sides with the porous coating.

22. The femoral stem prosthesis of claim 21, including an upper step between the porous coating and the neck along the medial arc.

23. The femoral stem prosthesis of claim 21, wherein the porous coating extends outwardly about the anterior, the posterior, a lateral, and a medial sides of the prosthesis body adjacent the neck.

\* \* \* \* \*